United States Patent
Giger et al.

(10) Patent No.: US 8,262,702 B2
(45) Date of Patent: Sep. 11, 2012

(54) OSTEOSYNTHETIC CLAMP FOR ATTACHING A BONE ANCHOR TO A SUPPORT ROD

(75) Inventors: Lukas Giger, Basel (CH); Erwin Fluehler, Allschwil (CH); Roman Iselin, Miami, FL (US)

(73) Assignee: Synthes USA, LLC, West Chester, PA (US)

( * ) Notice: Subject to any disclaimer, the term of this patent is extended or adjusted under 35 U.S.C. 154(b) by 852 days.

(21) Appl. No.: 12/064,531

(22) PCT Filed: Aug. 23, 2005

(86) PCT No.: PCT/EP2005/009101
§ 371 (c)(1),
(2), (4) Date: Mar. 13, 2009

(87) PCT Pub. No.: WO2007/022790
PCT Pub. Date: Mar. 1, 2007

(65) Prior Publication Data
US 2011/0098753 A1    Apr. 28, 2011

(51) Int. Cl.
*A61B 17/70*    (2006.01)
(52) U.S. Cl. .......... 606/252; 606/246; 606/251
(58) Field of Classification Search ............ 606/246, 606/305, 250, 264, 267, 277, 251, 252; 623/17.11, 623/17.15
See application file for complete search history.

(56) References Cited

U.S. PATENT DOCUMENTS

| 5,047,029 A | | 9/1991 | Aebi et al. ............. 606/61 |
| 5,261,909 A | * | 11/1993 | Sutterlin et al. ........ 606/264 |
| 5,344,422 A | | 9/1994 | Frigg ..................... 606/61 |
| 5,368,594 A | * | 11/1994 | Martin et al. ........... 606/252 |
| 5,501,684 A | | 3/1996 | Schlapfer et al. ....... 606/73 |
| 5,569,246 A | * | 10/1996 | Ojima et al. ........... 606/252 |
| 5,611,800 A | | 3/1997 | Davis et al. ............ 606/61 |
| 5,613,968 A | | 3/1997 | Lin ...................... 606/61 |

(Continued)

FOREIGN PATENT DOCUMENTS

DE    92 15 561.8    1/1993

(Continued)

OTHER PUBLICATIONS

International Search Report for PCT/EP2005/009101 dated Jun. 7, 2006.

(Continued)

*Primary Examiner* — Thomas J Sweet
*Assistant Examiner* — Seema Swaminathan
(74) *Attorney, Agent, or Firm* — Stradley, Ronon, Stevens & Young, LLP (57) ABSTRACT

An osteosynthetic clamp is provided for use in attaching a bone anchor to a support rod. The clamp comprises a carrier with a first portion adapted for connection to the anchor and with a second portion for connection to the rod. A clamping hook defines a bight in which the rod can be located and a head that passes through an aperture defined by the second portion of the carrier. The head of the hook passes through a collar, which is attached to the second portion of the carrier by engaging, complementarily shaped parts. These parts are defined respectively by the second portion of the carrier and by the collar and together form a joint permitting sliding translational movement of the collar relative to the carrier. A fastener can be secured to the head of the clamping hook and tightened in order to clamp the rod within the bight.

11 Claims, 6 Drawing Sheets

U.S. PATENT DOCUMENTS

| | | | |
|---|---|---|---|
| 5,624,441 A | 4/1997 | Sherman et al. | 606/61 |
| 5,667,506 A * | 9/1997 | Sutterlin | 606/252 |
| 5,885,285 A | 3/1999 | Simonson | 606/61 |
| 5,938,663 A | 8/1999 | Petreto | 606/61 |
| 6,187,005 B1 | 2/2001 | Brace et al. | 606/61 |
| 6,187,008 B1 | 2/2001 | Hamman | |
| 6,352,537 B1 * | 3/2002 | Strnad | 606/276 |
| 6,610,063 B2 * | 8/2003 | Kumar et al. | 606/250 |
| 6,626,906 B1 | 9/2003 | Young | 606/61 |
| 7,104,992 B2 | 9/2006 | Bailey | 606/61 |
| 7,166,109 B2 | 1/2007 | Biedermann et al. | 606/61 |
| 7,666,207 B2 * | 2/2010 | Schlapfer et al. | 606/246 |
| 8,002,808 B2 * | 8/2011 | Morrison et al. | 606/280 |
| 2003/0125742 A1 * | 7/2003 | Yuan et al. | 606/61 |
| 2004/0092930 A1 | 5/2004 | Petit et al. | 606/61 |
| 2004/0177847 A1 * | 9/2004 | Foley et al. | 128/95.1 |
| 2004/0254574 A1 | 12/2004 | Morrison et al. | 606/61 |
| 2005/0096654 A1 | 5/2005 | Lin | 606/61 |
| 2005/0228382 A1 | 10/2005 | Richelsoph et al. | 606/61 |
| 2006/0052784 A1 * | 3/2006 | Dant et al. | 606/61 |
| 2006/0064091 A1 * | 3/2006 | Ludwig et al. | 606/61 |
| 2006/0167455 A1 | 7/2006 | Clement et al. | 606/61 |
| 2006/0206114 A1 | 9/2006 | Ensign et al. | 606/61 |
| 2011/0098753 A1 | 4/2011 | Giger et al. | |

FOREIGN PATENT DOCUMENTS

| | | |
|---|---|---|
| WO | 94/00066 | 1/1994 |

OTHER PUBLICATIONS

Synthes Spine: USS Fracture System Technique Guide (2001).

* cited by examiner

OSTEOSYNTHETIC CLAMP FOR ATTACHING A BONE ANCHOR TO A SUPPORT ROD

The present invention relates to an osteosynthetic clamp for use in attaching a bone anchor such as a bone screw or spinal hook to a support rod and to a fixation assembly incorporating same. The invention is particularly, but not exclusively, for implantation in the lumbar spinal region in and as a sacro-iliac fixation assembly.

Osteosynthetic clamps are typically implantable devices for use by surgeons in the treatment of deformities, skeletal instabilities, tumours, fractures and degenerative diseases. For example, in a sacro-iliac fixation assembly a support rod is secured by way of a variety of bone screws to various of the vertebrae making up the sacrum and to the ilium, as determined appropriate by the surgeon. The support rod may be linear or curvilinear, as appropriate and the fixation points of the screws may be connected to the rod using lateral connectors of various lengths.

EP 0 425 783, the teachings of which are incorporated herein by reference, discloses an implantable unilateral osteosynthetic clamp for attaching a pedicle screw or spinal hook to a single spinal support rod in which the axes of the screw and the support rod are in different planes and can be set at variable inclined angles. Means are provided to enable the distance between these two axes to be variable in the form of carrier defining a through slot, a receiving means for the support rod arranged movably within the through slot and a compression means for clamping the screw relative to the receiving means.

It is clearly an advantage when using such fixation assemblies for them to be capable of manipulation by the surgeon as easily as possible and for the clamps or other means used to secure the bone screws or other bone anchors employed as readily as possible to the support rod. Some prior art assemblies require the support rod to be threaded into place into the clamps along the longitudinal axis of the rod, for example the exterior surface of the support rod may be threaded to engage threads formed on a bight surface of the receiving means. In other assemblies the exterior surface of the rod may be grooved to engage with a similarly grooved surface of the bight of the receiving means. Hence, easy engagement of the support rod by the receiving means can be difficult to accomplish. It is also advantageous for the positions of the clamp and assembly to be easily adjustable in order that the surgeon can adapt it readily to provide the best 'fit' for any particular patient.

It is an object of the present invention to provide an osteosynthetic clamp for use in attaching a bone anchor to a support rod and to a fixation assembly incorporating same that facilitates fitment and that enables adjustments to be made in situ to suit a particular patient.

According to a first aspect of the present invention there is provided an osteosynthetic clamp for use in attaching a bone anchor to a support rod comprising a carrier with a first portion adapted for connection to a bone anchor and with a second portion for connection to a support rod; a clamping hook with a bight in which a support rod can be located and a head that passes through an aperture defined by the second portion of the carrier; a collar through which the head of the clamping hook passes and which is attached to the second portion of the carrier by engaging, complementarily shaped parts defined respectively by the second portion of the carrier and by the collar that together form a joint permitting sliding translational movement of the collar relative to the carrier; and a fastener that can be secured to the head of the clamping hook and tightened to press the carrier via the collar onto a support rod located in the bight of the clamping hook in order to clamp the support rod within the bight.

Such an osteosynthetic clamp has the advantage that it can be attached laterally to the support rod rather than the rod having to be directed into the clamp along its longitudinal axis. This greatly facilitates the fitment of the support rod in a fixation assembly. This is a considerable advantage for a clamp for implantation in the lumbar spinal region as the support rod often needs to be curvilinear along its longitudinal axis. It also means that the support rod itself can be of varied cross-section size and shape as it does not need to be capable of being directed into a plurality of clamps along the whole of its length, as would otherwise be the case. Generally, however, the support rod is between 5 mm and 6 mm in diameter and of circular cross section and the main advantages of having a laterally attachable clamp comes into play when 1. the end of the support rod cannot be accessed, for example, when the clamp is to be attached to an already implanted rod whose ends are covered by tissue; and/or
2. the clamp is to be attached to an already implanted rod between two bone screws when sliding on a clamp down the rod would be impossible.

Preferably, the aperture in the second portion of the carrier is elongate in order that a variable distance is possible between the clamped position of the support rod and the bone anchor.

Preferably also, the engaging, complementarily shaped parts defined by the collar and the second portion of the carrier form a sliding joint along the length of the elongate aperture. In a preferred embodiment, these complentarily shaped parts comprise a dovetail and a complementarily-shaped recess. The carrier may define the dovetail and the collar may define the complementarily-shaped recess or vice versa.

Preferably also, the head of the clamping hook is threaded and the fastener comprises a nut which can be screwed on the threaded head Advantageously, the carrier is pressed against the collar via bearing faces that at least in part are angled with respect to a surface normal to the direction of the compressing force of the fastener. This provides an increased rotational stability along the axis of the clamps. In some embodiments, the bearing faces are at an angle of between about 5° and about 60° with respect to the surface normal to the direction of the compressing force of the fastener. In further embodiments, the bearing faces are at an angle of between about 15° and 45°. In a preferred embodiment, the bearing faces are angled at about 15° with respect to a surface normal to the direction of the compressing force of the fastener.

Preferably also, the collar defines an elongate recess in which the support rod is located and is clamped therein by the clamping hook.

In some embodiments of the present invention, the first portion of the carrier defines a socket for receiving a head portion of the bone anchor. In further embodiments, a surface of the socket defines a part-spherical seat against which an at least part spherical portion of the head of the bone anchor can bear in order that the bone anchor can be secured at one of a plurality of different angles relative to the carrier. Such arrangements are described in detail in EP 0 599 847.

In other embodiments, the first portion of the carrier defines an aperture in which is secured a collet that is clamped around a head portion of the bone anchor. In such an embodiment the head portion of the bone anchor is preferably substantially spherical and the collet defines a recess with a part-spherical surface in which the head portion of the bone anchor is located in order that the bone anchor can be secured at one of a plurality of different angles relative to the carrier. Preferably, the aperture in the first portion of the carrier has a conical surface and at least a part of an exterior surface of the collet has a complementary conical or part-spherical surface. In such an embodiment the collet is preferably secured to the carrier by a nut that when tightened pulls the collet into the aperture in order that pressure is exerted by the carrier on the head portion of the bone anchor via the collet in order to clamp the bone anchor in position.

Preferably also, the first and second portions of the carrier are angled with respect to one another.

According to a second aspect of the present invention there is provided a fixation assembly including an osteosynthetic clamp according to the first aspect of the invention and comprising a bone anchor connected to the first portion of the carrier of the clamp and a support rod connected to the second portion of the carrier of the clamp.

The bone anchor is preferably a bone screw that preferably has a thread adapted to compress cancellous bone tissue.

The various aspects of the present invention will now be described by way of example with reference to the accompanying drawings, in which.

As shown in FIGS. 1 to 4, an osteosynthetic clamp according to the invention is used to attach a bone anchor 1 such as a bone screw (as shown) to a support rod 2. The clamp comprises, in combination, a carrier 3, a clamping hook 4, a collar 5, and a fastener 6 as will now be described in detail.

Figure 9:
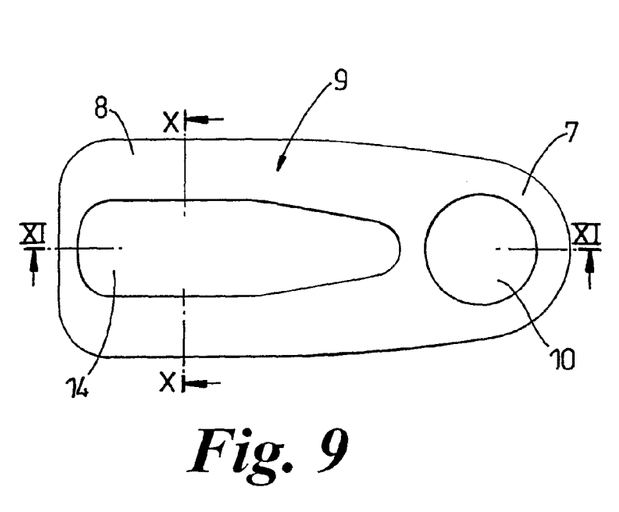
FIG. 9 is a top view of a carrier forming part of an osteosynthetic clamp similar to that shown in FIGS. 1 to 4 but in this case being of planar construction.
Figure 10:
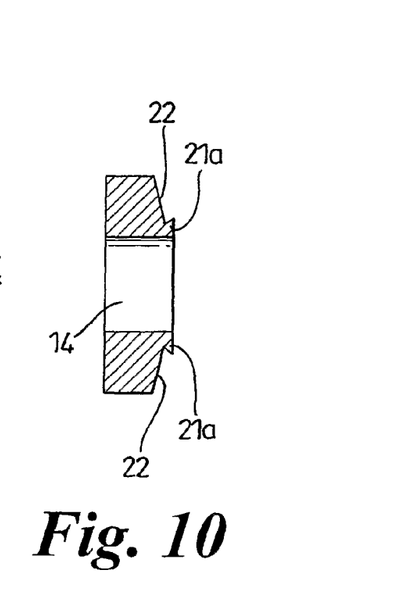
FIG. 10 is a cross-sectional view of the carrier along the line X-X in FIG. 9.
Figure 11:
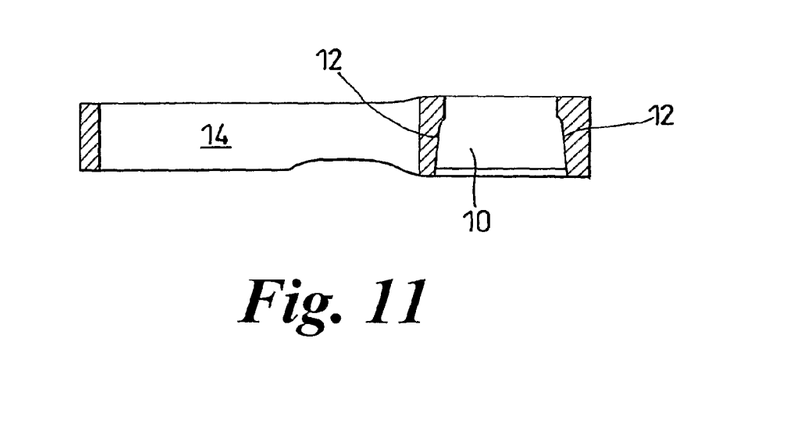
FIG. 11 is a cross-sectional view of the carrier along the line XI-XI in FIG. 9.

The carrier 3 comprises a first portion 7 adapted for connection to the bone anchor 1 and a second portion 8 adapted for connection to the support rod 2. The carrier 3 shown in FIGS. 1 to 4 has its first portion 7 angled with respect to its second portion 8. However, a carrier 9, as shown in FIGS. 9 to 11, is a modification wherein the first and second portions 7 and 8 occupy the same plane. It will be appreciated that the first and second portions 7 and 8 of the carrier can be angled more or less steeply as required by a surgeon. It will also be appreciated by those skilled in the art that the two portions 7, 8 of the carrier 3 can be angled in any desired direction.

The first portion 7 of the carrier 3, 9 defines a socket 10 for receiving a head portion 11 of the bone anchor 1. In some embodiments, the socket 10 defines a part-spherical seat 12 against which an at least part spherical surface portion 13 of the head 11 of the bone anchor 1 can bear. This enables the bone anchor 1 to be secured at one of a plurality of different angles relative to the carrier 3, 9. The clamp therefore permits a surgeon to adjust the fixation angle of each bone anchor 1 to the specific configuration required by a particular patient. However, it is important that after fitment the angle between the bone anchor 1 and the carrier 3, 9 does not vary. The surfaces of the seat 12 and/or the part-spherical surface portion 13 of the head 11 of the anchor 1 may therefore be roughened to provide a better grip therebetween to reduce the likelihood of relative movement. An embodiment describing an alternative method of attaching the bone anchor 1 to the first portion 7 of the carrier 3, 9 is described below with reference to FIG. 12.

The second portion 8 of the carrier defines an aperture 14 which can accommodate a head 15 of the clamping hook 4. The aperture 14 is preferably elongate in order that the position of the clamping hook 4 relative to the carrier 3, 9 can be varied. As the position of the clamping hook 4 determines the position of the support rod 2, this enables the distance between the bone anchor 1 and the support rod 2 to be regulated and adjusted individually for each patient. It will also be appreciated that the carrier 3, 9 can be made in a range of different lengths, again to suit different bone anchor attachment sites within the body, in particular within the lumbar region of the spine and pelvis.

Figure 5:
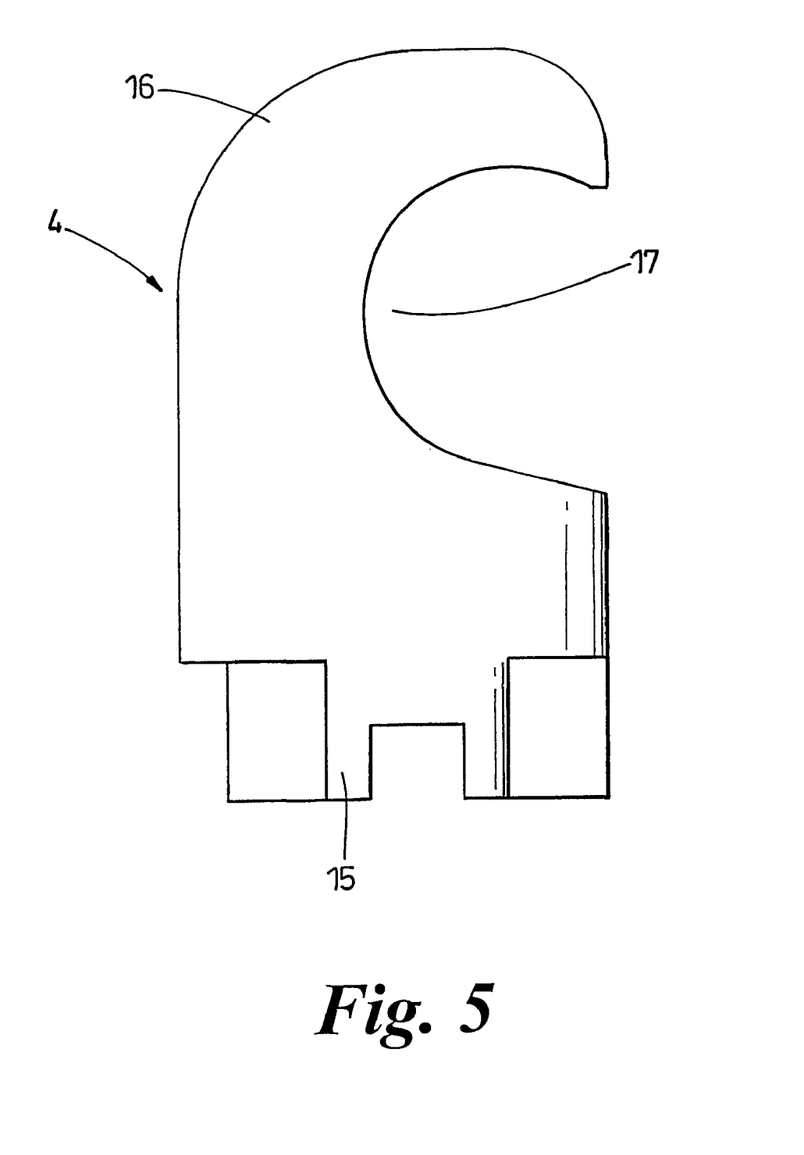
FIG. 5 is a side view, to an enlarged scale, of a clamping hook forming part of the osteosynthetic clamp shown in FIGS. 1 to 4.

As shown in particular in FIG. 5, the clamping hook 4 which cooperates with the carrier 3, 9 comprises a hooked portion 16 defining a bight 17 in which the support rod 2 can be located and the head 15 that passes through the aperture 14. The bight 17 can be of a sufficient size and shape to accommodate particular sizes of support rods 2 for use in different patients and for different forms of fixation assemblies. The head 15 is preferably externally threaded so that the fastener 6 can comprise a nut which can be simply screwed on to the head 15 and tightened to secure the clamping hook 4 in position, as further described below.

Figure 6:
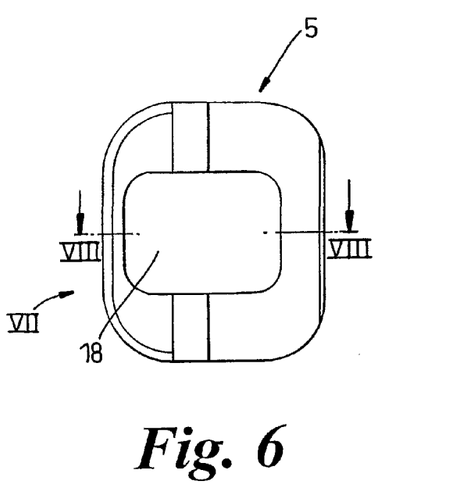
FIG. 6 is a view from below of a collar forming part of the osteosynthetic clamp shown in FIGS. 1 to 4.

Located between the support rod 2 when inserted into the bight 17 of the clamping hook 4 and the carrier 3 is the collar 5. As shown in detail in FIGS. 6 to 8, the collar comprises a central aperture 18 through which the head 15 of the clamping hook 4 passes before it passes through the aperture 14 in the carrier 3, 9. On the side of the collar 5 adjacent the bight 17 of the clamping hook 4, is an elongate recess 19 in which the support rod 2 can locate and is clamped therein on its opposite side by the hooked portion 16 of the clamping hook 4. The other side 20 of the collar 5 adjacent the carrier 3 is adapted for attachment to the carrier 3. To this end, the side edges of the aperture 14 on the side of the carrier 3 adjacent the collar 5 and the side 20 of the collar 5 are provided with engaging complementarily shaped parts 21a, 21b that together form a joint permitting sliding translational movement of the collar 5 relative to the carrier 3. These complementarily shaped parts 21a, 21b are such that they form a sliding joint along the complete length of the elongate aperture 14 so that the collar can be readily positioned at any location along the length of the aperture 14 to vary the distance between the bone anchor 1 and the support rod 2 to be regulated and adjusted, as aforesaid.

Such a sliding joint arrangement is a considerable advantage over prior art arrangements as it retains the relative position of the clamping hook 4 and therefore of the support rod 2 relative to the bone anchor 1 whilst a simple sliding adjustment is made by the surgeon to space the support rod 2 at the desired distance from the bone anchor 1.

Figure 1:
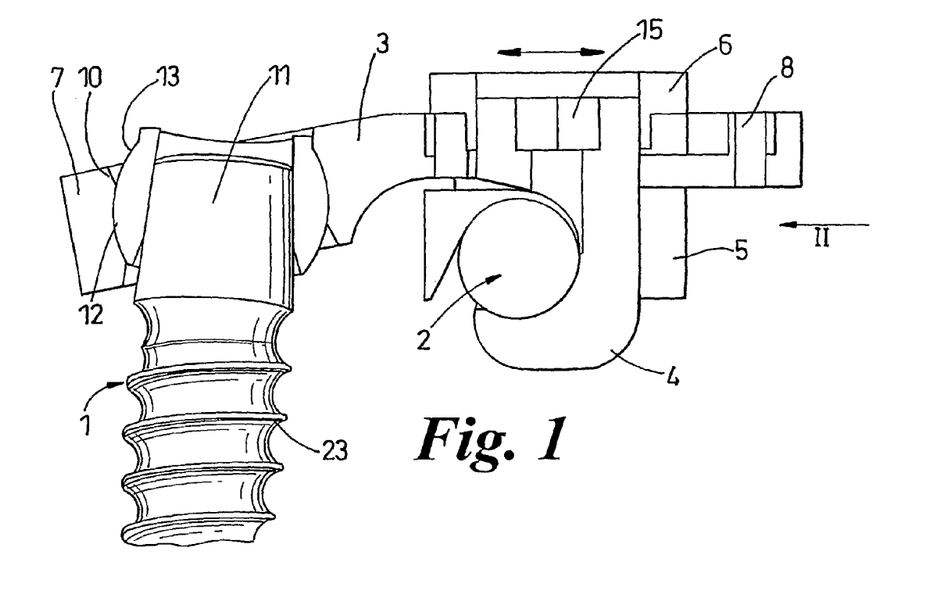
FIG. 1 is a side view, in partial cross-section, of an osteosynthetic clamp according to the first aspect of the present invention in use in a fixation assembly according to the second aspect of the invention.
Figure 2:
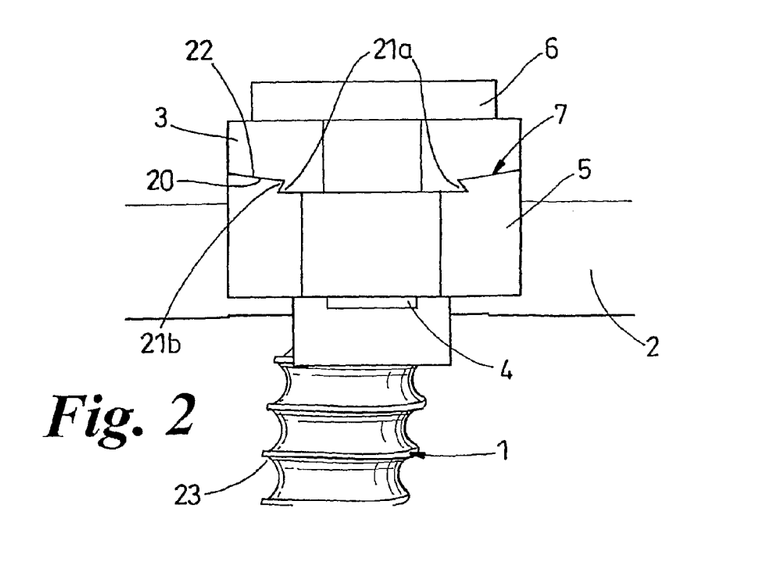
FIG. 2 is an end view in the direction of arrow II in FIG. 1.
Figure 3:
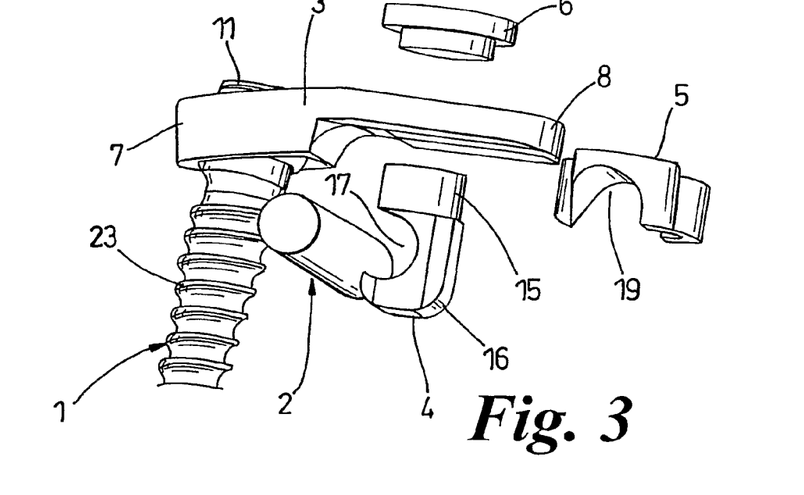
FIGS. 3 and 4 are perspective, exploded views of the assembly shown in FIGS. 1 and 2 from slightly different viewpoints and to a slightly reduced scale.
Figure 4:
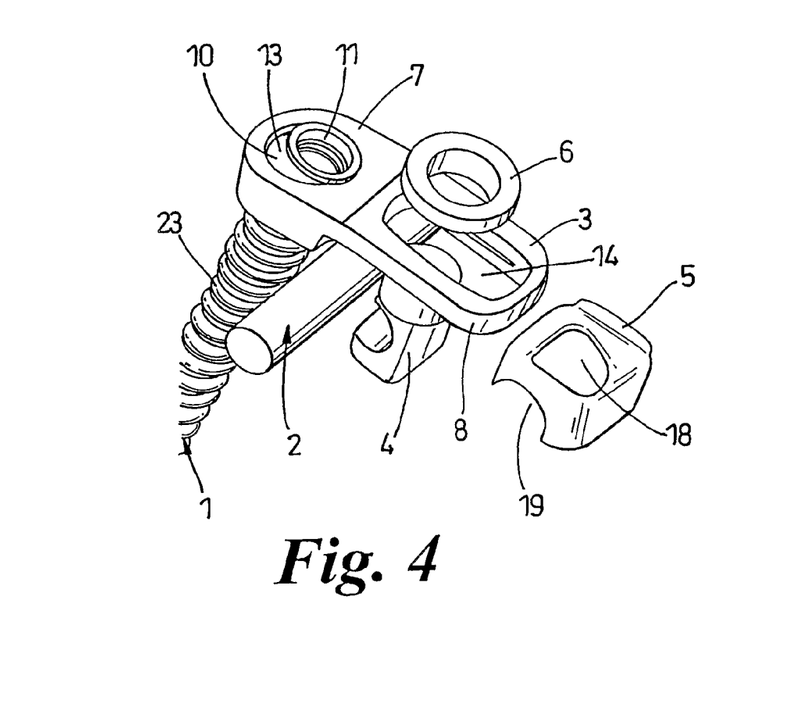
Figure 7:
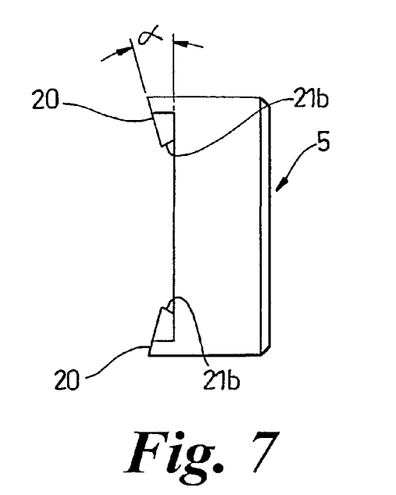
FIG. 7 is an end view of the collar in the direction of arrow VII in FIG. 6.
Figure 8:
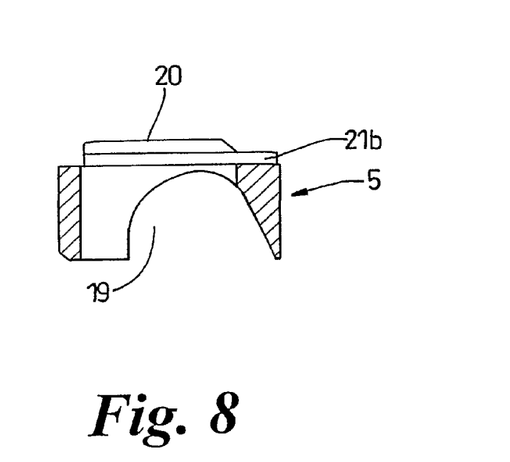
FIG. 8 is a cross-sectional view of the collar along the line VIII-VIII in FIG. 6.

As shown in FIG. 2 and in detail in FIGS. 7 and 10, the shaped parts 21a, 21b comprise a dovetail 21a and a complementarily-shaped recess 21b. In the present illustrated example, the carrier 3 defines the dovetail 21a and the collar 5 defines the complementarily-shaped recess 21b. It will be appreciated, however, that this could be the other way around. Also, it will be appreciated that the complementarily shaped parts 21a, 21b could be fashioned into other shapes than a dovetail and similar recess. The main purpose of the dovetail 21a is to prevent the collar 5 from being detached from the carrier 3 during handling, mechanical resistance being provided by means of the angled bearing surfaces 21a, 21b. Simple tongue and groove arrangements could be used as an alternative but the dovetail shape has the additional advantage that when the fastener 6 is tightened, as described below, the collar 5 is more firmly retained in position in relation to the carrier 3. This is most important in an implanted assembly because subsequent tightening can not be readily carried out.

In order to increase the mechanical resistance against rotation of the arrangement, the parts of the bearing face 20 of the collar 5 on each side of the recess 21b and the parts of the face 22 of the carrier 3 on either side of the aperture 14 adjacent the dovetail parts 21a are angled at an angle $\alpha$ with respect to a surface normal to the direction of the compressing force of the fastener 6. In some embodiments, the bearing faces are at an angle $\alpha$ of between about 5° and about 60° with respect to the surface normal to the direction of the compressing force of the fastener. In other embodiments, the bearing faces are at an angle $\alpha$ of between about 15° and 45°. In a preferred embodiment, the bearing faces are angled at about 15° with respect to a surface normal to the direction of the compressing force of the fastener.

Figure 12:
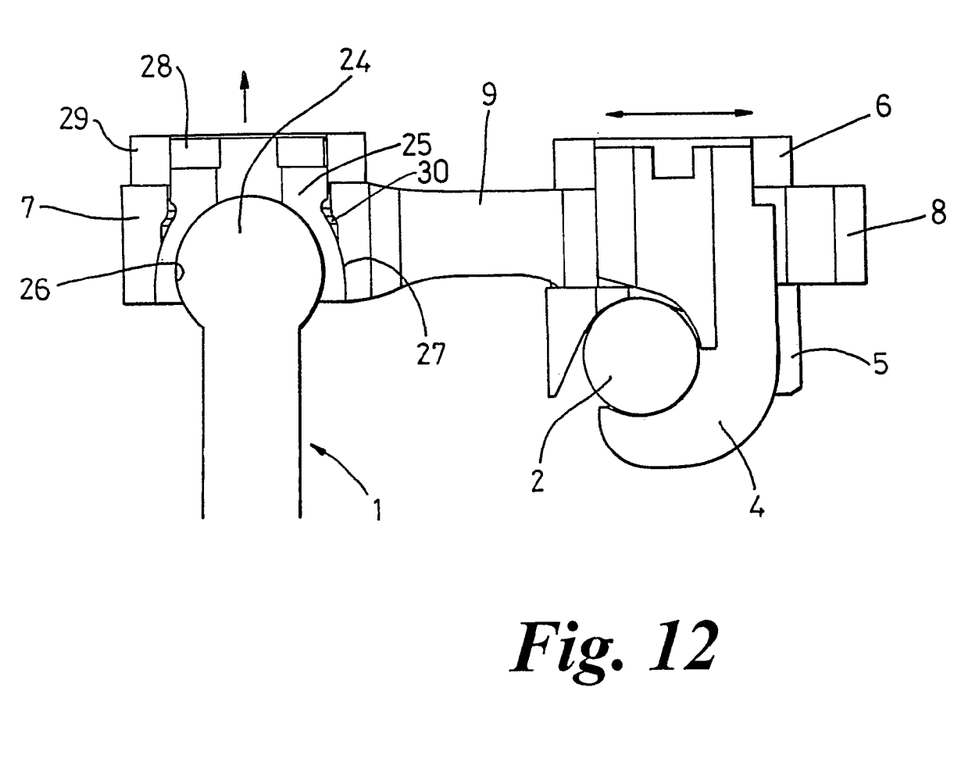
FIG. 12 is a view similar to FIG. 1 of another embodiment of osteosynthetic clamp.

Turning now to FIG. 12, this shows an osteosynthetic clamp similar to that described above with reference to FIGS. 1 to 4 but with a carrier 9, as shown in FIGS. 9 to 11, wherein the first and second portions 7 and 8 occupy the same plane. It should be appreciated, however, that either form of carrier 3, 9 could be used. In this embodiment, the manner in which the bone anchor 1 is secured to the carrier 9 is different to that shown in FIG. 1. Here, the bone anchor 1, which again comprises a bone screw, is provided with a substantially spherical head 24 that is located in a collet 25. The collet 25 has a recess with a part-spherical surface 26 in which the head 24 of the anchor 1 is engaged. The exterior surface 27 of this recessed portion of the collet 25 is conical or part-spherical. The collet 25 is also provided with an outer surface portion 28 which is threaded and can be engaged by a fastener such as a nut 29. The collet 25 locates in an aperture 30 defined by the carrier 9 such that the threaded portion 28 projects in order that the nut 29 can be secured thereto and tightened to pull the collet 25 into the aperture 30. The aperture 30 is made with a conical surface that flares outwardly on the side of the carrier 9 from which the bone anchor 1 will project. The surfaces of the aperture 30 and the collet 25 are complementary in order that when the nut 29 is tightened to pull the collet 25 further into the conical aperture 30, pressure is exerted by the carrier 9 on the head 24 of the anchor 1 via the collet 25 in order to clamp the anchor 1 in position. It will be appreciated, however, that before such tightening the longitudinal axis of the anchor 1 can be adjusted with respect to the position of the carrier 9 by rotation of the head 24 within the recess of the collet 25. The anchor 1 is then clamped in this position. The osteosynthetic clamp is therefore polyaxial.

It will be appreciated that in use, the osteosynthetic clamp according to the invention is first attached to the bone anchor 1 and secured to an appropriate part of a patient's skeletal structure. As the clamp is particularly adapted for implantation in the lumbar spinal region to form part of a sacro-iliac fixation assembly, the bone anchor is likely to be a bone screw comprising either a sacral screw or an iliac screw. Such screws, which are usually of different lengths, are preferably colour coded to prevent errors from occurring. Also, such screws preferably have a thread 23 adapted to compress cancellous bone tissue so that there is a good purchase with the bone tissue and they are held tightly in position. Once the bone anchor 1 and attached clamp has been secured to the patient it can then be secured to the support rod 2. With the fastener 6 untightened, the collar 5 can be moved relative to the carrier 3 by virtue of the sliding joint formed by the engaging complementarily shaped parts 21a, 21b. The collar 5 is moved so that the rod 2 is engaged within the recess 19 of the collar above the bight 17 of the clamping hook 4. Final spacing adjustments to the distance between the bone anchor 1 and the support rod 2 can then be made by sliding the collar along the carrier 3. Once the surgeon is satisfied this distance is correct, the fastener 6 is then tightened. For example if the fastener 6 is a nut it is screwed down onto the threaded head 15 of the hook 4. On tightening of the fastener 6, the hooked portion 16 of the clamping hook 4 is moved relatively towards the collar 5 and the carrier 3 is pressed via the collar 5 onto the rod 2 which is thereby clamped within the bight 17.

As indicated above, one advantage of this method of fitment is that the clamp is attached laterally to the support rod 2 by a form of 'click on' fitment rather than having to direct the rod 2 into the clamp. This is a considerable advantage if the support rod 2 is curvilinear rather than straight, which is often the case in sacro-iliac fixation assemblies. Also, the clamp can accommodate a range of rod sizes and the diameter of the rod can therefore vary along its length without affecting its attachment to the clamp. The clamp is therefore particularly useful in fixation assemblies when the support rod is of this form or if it is advantageous for any other reason to have a non-uniform diameter along its length. The clamp can also be readily used in circumstances where the ends of an already implanted support rod cannot be readily accessed for the reasons described above.

The invention claimed is:

1. An osteosynthetic clamp for use in attaching a bone anchor to a support rod, the clamp comprising:
   a carrier with a first portion adapted for connection to the bone anchor and with a second portion adapted for connection to the support rod;
   a clamping hook, the hook including a bight wherein the bight is sized and configured to receive the support rod, and a head that passes through an elongate aperture in the second portion of the carrier;
   a collar located in-between the clamping hook and the carrier, and through which the head of the clamping hook passes, and which is attached to the second portion of the carrier by engaging, complementarily shaped parts defined respectively by the edges of the elongate aperture and by the collar that together form a joint permitting the collar to be longitudinally adjustable toward or away from the bone anchor by sliding the collar along the elongated aperture; and
   a fastener that can be secured to the head of the clamping hook and tightened to press the carrier via the collar against the support rod located in the bight of the clamping hook in order to clamp the support rod within the bight.

2. The clamp of claim 1, wherein the complementarily shaped parts defined by the edges of the elongate aperture and by the collar form a sliding joint along the length of the elongate aperture.

3. The clamp of claim 1, wherein the engaging, complementarily shaped parts comprise a dovetail and a complementarily-shaped recess.

4. The clamp of claim 3, wherein the carrier defines the dovetail and the collar defines the complementarily-shaped recess.

5. The clamp of claim 1, wherein the head of the clamping hook is threaded and the fastener comprises a nut which can be screwed on the threaded head.

6. The clamp of claim 1, wherein the carrier is pressed against the collar via bearing faces that at least in part are angled with respect to a surface normal to the direction of the compressing force of the fastener.

7. The clamp of claim 6, wherein the bearing faces are angled to the surface normal to the direction of the compressing force of the fastener in a range of between about 5 degrees and about 60 degrees.

8. The clamp of claim 1, wherein the collar includes an elongate recess sized and configured to receive the support rod.

9. The clamp of claim 1, wherein the first portion of the carrier defines a socket for receiving a portion of the bone anchor.

10. The clamp of claim 9, wherein a surface of the socket defines a part-spherical seat against which an at least part spherical portion of the portion of the bone anchor can bear in order that the bone anchor can be secured at one of a plurality of different angles relative to the carrier.

11. The clamp of claim 1, wherein the first and second portions of the carrier are angled with respect to one another.

* * * * *